United States Patent [19]

Kervennal et al.

[11] Patent Number: 4,478,757

[45] Date of Patent: Oct. 23, 1984

[54] PROCESS FOR THE MANUFACTURE OF AROMATIC ISOCYANATES

[75] Inventors: Jacques Kervennal, Lyons; Jean-Marie Cognion, Saint Genis Laval; Pierre Braunstein, Strasbourg, all of France

[73] Assignee: Produits Chimiques Ugine Kuhlmann, Courbevoie, France

[21] Appl. No.: 437,810

[22] Filed: Oct. 29, 1982

[30] Foreign Application Priority Data

Nov. 3, 1981 [FR] France ................................ 81 20567

[51] Int. Cl.³ ........................................... C07C 118/06
[52] U.S. Cl. ............................................. 260/453 PC
[58] Field of Search .................................. 260/453 PC

[56] References Cited

U.S. PATENT DOCUMENTS 3,674,827 6/1972 Lao et al. ..................... 260/453 PC
3,714,216 6/1973 Schnabel et al. .............. 260/453 PC Primary Examiner—Dolph H. Torrence
Attorney, Agent, or Firm—Sigalos & Levine

[57] ABSTRACT

A process for the manufacture of aromatic isocyanates by carbonylation of nitro derivatives comprising carrying out the reaction in the presence of supported catalysts containing as the active phase particles or an oxide of a precious metal of Group VIII and of a metal selected from Group $V_B$, $VI_B$, and VIII of the Periodic Table; the precursor of the active phase being a heteropolymetallic complex and, more particularly, a mixed bimetallic cluster.

7 Claims, No Drawings

PROCESS FOR THE MANUFACTURE OF AROMATIC ISOCYANATES

BACKGROUND OF THE INVENTION

The present invention concerns a process for the manufacture of organic isocyanates from nitro compounds and more specifically a process for the preparation in the liquid phase of aromatic isocyanates by reaction between aromatic nitro derivatives and carbon monoxide in the presence of heterogeneous catalysts constituted of metallic particles or metallic oxides, deposited on supports, originating from heteropolymetallic complexes.

Aromatic isocyanates are organic intermediates of great interest. Two among them have been particularly well developed; namely, toluene diisocyanate and diphenylmethane-4,4'-diiosocyanate which are used in the synthesis of polyurethanes. Certain substituted aromatic isocyanates are likewise used in the syntheses of herbicides. Industrial processes for the preparation of these products all involve the phosgenation reaction of an amine originating from the catalytic hydrogenation of a nitro derivative. The drawbacks of these processes are several. More particularly, they necessitate the synthesis and manipulation of phosgene, a very dangerous product, and they produce important quantities of hydrochloric acid as a by-product requiring the installation and costly upkeep of a special shop for the electrolysis of this acid in order to recycle the chlorine and hydrogen.

The advantage which a process avoiding the use of phosgene presents is obvious. Several patents describe catalytic compositions making it possible to prepare the isocyanates at elevated temperature and pressure by reaction of an organic nitro compound with carbon monoxide. The favorable role of noble metals for this reaction is well known from these publications. Thus, French Pat. No. 1,600,529 describes the use of a precious metal halide as a catalyst, in the presence of a basic amine of aromatic character. German Pat. No. 1,910,303 describes catalysts formed of halides or oxides of Ru, Rh, Pd, Os, Ir, Pt, and of a heteroatomic sulfur-containing compound, possibly in the presence of an oxide of Cr, Mo, Nb, W, V. French Pat. No. 1,567,321 describes the use of a catalytic system formed by a precious metal halide and an organic phosphorous compound; for instance a triaryl phosphine or a phosphite. French Pat. No. 2,155,242 describes catalytic systems consisting of one or several palladium and/or rhodium halides, one or several basic heteroatomic nitrogen compounds, and a co-catalyst formed by one or several iron borates. In French Pat. No. 2,120,110, besides a palladium halide and heterocyclic nitrogen-containing bases, the catalytic formulation includes a co-catalyst consisting of one or several iron and/or manganese molybdates.

All of these systems based on noble metals make it possible to produce isocyanates from nitro compounds with variable selectivities and productivities. However, the difficult and costly recovery of the isocyanates prevents their industrial use.

Certain attempts have been made to deposit the active phases on supports. It is, thus, that in French Pat. Nos. 1,600,529 and 1,558,896, as well as in U.S. Pat. No. 3,728,370, it has been envisioned, without practical illustration, to deposit the catalyst on supports of the following types: alumina, silica, carbon, barium sulfate, calcium carbonate, asbestos, bentonite, diatomaceous earth, fuller's earth. British Pat. No. 1,257,932 describes the use of palladium, palladium chloride, or rhodium chloride on alumina, silica and silicon carbide for carbonylation, in the vapor phase, of nitro derivatives. A publication of W. B. HARDY and R. P. BENNETT in Tetrahedron Letters No. 1, p. 961 (1967) gives the results obtained with a carbonylation of nitrobenzene yielding phenylisocyanate.

Supported catalysts, whose active phase consists of both palladium and molybdenum, are known. Thus, French Pat. No. 2,452,318 describes the carbonylation of aromatic nitro compounds with the help of catalysts consisting of palladium and molybdenum oxides deposited by successive impregnation of ammonium molybdate and palladium chloride on an alumina, silica, or silica/alumina support.

SUMMARY OF THE INVENTION

It has been discovered that the use, as precursors, of the active phase of hetero-polymetallic molecular complexes, that is to say systems containing metallic atoms of different nature, leads to catalysts whose performances in the carbonylation of aromatic nitro compounds are very considerably improved.

Briefly, the present invention comprises carrying out the manufacture of aromatic isocyanates by carbonylation of nitro derivatives in the presence of a supported catalyst containing as the active phase particles or an oxide of a precious metal of Group VIII and of a metal selected from Group $V_B$, $VI_B$, or VIII of the Periodic Table; the precursor of the active phase being a heteropolymetallic complex.

DETAILED DESCRIPTION

The supported catalysts used in the present invention require the use of a heteropolymetallic complex.

These complexes contain a precious metal of Group VIII and a second metal of Group $V_B$, $VI_B$, or VIII of the Periodic Table. The mixed bimetallic clusters are good examples, according to the invention, of such molecular species. These complexes consist of a polymetallic core in which direct interactions exist between the atoms of different metals; the atomic ratio of the metals can vary from one molecule to another. In the organometallic clusters, this core is surrounded by coordinates (coordination compounds), among which there are, in nonlimiting fashion, carbon monoxide, aliphatic or aromatic phosphines, unsaturated organic ligands such as cyclopentadienyls.

Among the favorably associated couples there are the following metals: palladium/molybdenum, platinum/molybdenum, palladium/iron, platinum/iron, palladium/tungsten, platinum/tungsten.

As nonlimiting examples of such clusters, there is $Pd_2Mo_2(\eta^5-C_5H_5)_2(CO)_6(PEt_3)_2$ whose synthesis has been described by R. BENDER, P. BRAUNSTEIN, Y. DUSAUSOY and J. PROTAS in Angew. Chem. Int. Ed. Engl. 1978, 17, 596. There is also $Pt_2Mo_2(\eta^5-C_5H_5)_2(CO)_6(PEt_3)_2$ and $Pt_2W_2(\eta^5-C_5H_5)_2(CO)_6(PPh_3)_2$ described by P. BRAUNSTEIN et al. in the Journal of Organometallic Chem. 1979, vol. 172, $C_{51}$.

They are generally soluble in different organic solvents, and chlorinated solvents such as methylene chloride or chloroform are preferentially used.

Heteropolymetallic molecular complexes can be deposited on various supports according to impregnation techniques in order to lead to the catalysts used according to the invention.

Thus, the support, placed under nitrogen, can be covered, for instance, with a solution of the cluster in an organic solvent such as methylene chloride; the whole unit is then degassed under vacuum and the solvent distilled.

Another technique consists in placing the support into a rotary evaporator which is constantly and regularly agitated and in sprinkling it, for instance, with a solution of the cluster in an organic solvent, under such temperature and pressure conditions that the latter is evaporated (in proportion) as it is being introduced.

After drying, the impregnated support is heated to at least 300° C. under nitrogen with the help of a linear temperature programming at a rate of 2° C./min. in order to decompose the metallic complex in the form of metal or oxide particles.

The supports which can be utilized are various; in a nonlimiting fashion we can cite silicas, aluminas, silica-aluminas, magnesium oxide, and the like.

The impregnation can be carried out in such a way as to lead to metal concentrations on the support of 0.1 to 20% by weight and preferentially between 1 and 15%.

The nitro compounds are placed in contact with carbon monoxide at elevated temperature and pressure in the presence of the catalyst prepared according to the operating method described above. It is possible to operate in the presence of an organic solvent, by a discontinuous technique in equipment of the autoclave type or by a continuous technique which makes it possible to eliminate the isocyanate produced as soon as it is formed. The reaction equation can be written according to the following scheme:

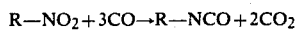

$$R-NO_2 + 3CO \rightarrow R-NCO + 2CO_2$$

The process according to the invention is applicable to aromatic compounds including one or several nitro groups attached to a carbon atom of aromatic nucleus. These compounds, known as base materials in the preparation of aromatic mono- and diisocyanates, can be represented by the formula:

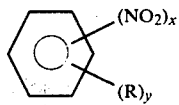

in which $x=1$ or 2 and $y=0$, 1, 2, 3, with R being a group of atoms or an atom attached to the aromatic nucleus and representing an alkyl group having 1 to 10 carbon atoms, a halogen atom, chlorine or bromine for instance, or an alkoxy group OR' in which R' is an alkyl radical having 1 to 10 carbon atoms. Nonlimiting examples of aromatic compounds having one or several nitro groups, which can be used according to the invention, are nitrobenzene, ortho-nitro-toluene, para-nitrotoluene, 1,2-dinitrobenzene, 1,3-dinitrobenzene, 1,4-dinitrobenzene, 2,4-dinitrotoluene, 2,6-dinitrotoluene, 1-methoxy-2,4-dinitrobenzene, 1-chloro-2-nitrobenzene, 1-chloro-2-4-dinitrobenzene, 3,4-dichloronitrobenzene, 2-chloro-4-nitrotoluene, 3-chloro-4-bromonitrobenzene, and the like.

The process according to the invention is likewise applicable to aromatic nitro compounds possessing several nuclei which are substituted with one or several nitro groups and possibly with one or several halogen atoms and/or one or several alkyl groups such as, for instance, as nonlimiting examples, dinitrodiphenylmethane, 2,4'-dinitro stilbene, 4,4'-dinitrostilbene, 2,4'-dinitrobibezyl, 4,4'-dinitrobibenzyl.

The concentration of catalyst in the reaction medium expressed by the ratio of the number of gram atoms of precious metal to the number of nitro groups to be transformed can vary between $10^{-4}$ and 1 and preferably between $5 \times 10^3$ and $10^{-1}$.

The reaction can be carried out in the absence of solvent, but the presence of a solvent generally promotes the isocyanate selectivity. The solvents preferably used are saturated or aromatic hydrocarbons such as hexane, heptane, n-decane, decalin, benzene, toluene or xylene and aromatic hydrocarbons such as chlorobenzene and the dichlorobenzenes. Fluorinated (fluorine-containing) solvents such as perfluorinated methyldecalin or trichlorotrifluoroethane.

When the operation takes place in the presence of a solvent, the proportion is not critical, but operation generally takes place with solutions containing from 5 to 50% by weight of the nitro derivative in the solvent. It is recommended to add to the reaction medium quantities of pyridine ranging from 0.1 to 30 moles per mole of nitro derivative and preferably from 0.5 to 10 moles per mole of nitro derivative for the purpose of improving isocyanate selectivities.

The reaction temperatures are between 100° C. and 500° C. and more specifically between 150° C. and 300° C. according to the nature and the stability of the reactants brought under the operating conditions.

The reaction pressures are between 20 and 500 bars, preferably between 150 and 350 bars, and must be sufficiently high in order to maintain a large fraction of the reactants in the liquid phase and to introduce a total quantity of carbon monoxide corresponding to a molar ration of $CO/NO_2$ group generally between 3 and 100 and preferably between 10 and 65.

The process of the invention is of particular interest for the manufacture of toluene diisocyanate and of phenyl isocyanate which, when cazbamated with a low molecular weight alcohol such as methanol or ethanol, can serve as base material for the manufacture of diphenylmethane-4,4'-diisocyanate according to the description given in Chemical Week, p. 57 of Nov. 9, 1977.

The invention will be described in connection with the examples which follow which are set forth for purposes of further illustration only.

The tests described in the following examples were carried out in discontinuous manner in 500-ml capacity autoclave made of Hastelloy C, equipped with a magnetic agitation device and capable of operating under pressures of up to 500 bars and temperatures of 300° C. The autoclave, charged with the different reactants, the possible solvent and the catalyst, is then flushed with nitrogen before being placed under carbon monoxide pressure at ordinary temperature. The autoclave is heated to the selected temperature and the progress of the reaction is controlled by recording the pressure. Following reaction, the isocyanate concentrations were evaluated by chemical determination with dibutylamine, and the concentrations of residual nitro derivatives and possibly of azo derivative were evaluated by vapor phase chromatography.

After reaction, the catalyst can easily be recovered by filtration. It can be recycled as is or undergo a regeneration treatment prior to reuse.

The results indicated are understood to have the following definitions:

T.T.G., the overall conversion rate =

$$\frac{\text{number of moles of nitro derivative converted}}{\text{number of moles of nitro derivative introduced}} \times 100$$

Isocyanate selectivity =

$$\frac{\text{number of moles of isocyanate formed}}{\text{number of moles of nitro derivative converted}} \times 100$$

Isocyanate yield =

$$\frac{\text{number of moles of isocyanate formed}}{\text{number of moles of nitro derivative introduced}} \times 100$$

EXAMPLE 1

3.5 g of a pure alumina sold commercially by CONDEA CHEMIE, having a specific surface of 250 m²/g and crushed into particles from 200 to 600 μm are placed into a spherical flask having a 50-ml capacity and mounted on an evaporator. 20 ml of a deoxygenated solution of 1 g of the mixed cluster of $Pd_2Mo_2(\eta^5-C_5H_5)_2(CO)_6(PPh_3)_2$ in methylene chloride are poured into the spherical flask having previously been flushed with nitrogen. The cluster was prepared according to the operating method by BRAUNSTEIN et al. in Angew. Chem. Int. Ed. Engl., 1978, 17, 596.

The solvent is distilled under reduced pressure and, after drying, the impregnated support is transferred, under nitrogen, into a firing tube whose temperature is progressively raised at a rate of 2° C./min. up to 300° C. Analysis indicates that the catalyst having thus been prepared contains 2.5% of palladium and 3% of molybdenum.

EXAMPLE 2

1.8 g of the catalyst prepared according to Example 1, 10 g of nitrobenzene and 1 g of pyridine are placed into the 500-ml capacity autoclave, made of Hastelloy C, which was previously described, and the total volume is made up to 100 ml with the addition of ortho-dichlorobenzene. After flushing with nitrogen, some carbon monoxide is compressed to a pressure of 200 bars at 200° C. The autoclave is insulated and heated, under agitation, to 240° C. for 70 minutes. Cooling is allowed to take place and the mixture is analyzed. The overall conversion rate amounts to 100% and the phenylisocyanate selectivity is 71%.

EXAMPLE 3

10 g of nitrobenzene, 5 g of pyridine, and 1.9 of the catalyst prepared in Example 1 are introduced into the autoclave used in Example 2 and the total volume is made up to 100 ml by means of ortho-dichlorobenzene. After flushing the reactor with nitrogen, the autoclave is placed under a pressure of 200 bars of carbon monoxide. Then, after having insulated it, the temperature is raised to 220° C., while the mixture is being agitated. After 4 hours of reaction time, the heating is cut off and the contents of the reactor are analyzed. The T.T.G. of nitrobenzene amounts to 100% and the phenylisocyanate selectivity to 80%.

EXAMPLE 4

3.5 g of alumina identical to the alumina used in Example 1 and crushed into particles of 200 to 600 μm are placed into a spherical flask for solids mounted on a rotary evaporator. The support is allowed to degasify for 15 minutes under a partial pressure of 100 mm of mercury. A deoxygenated solution of 1 g of cluster $Pd_2Mo_2(\eta^5-C_2H_5)_2(CO)_6(PPh_3)_2$ in 20 ml of methylene chloride is then introduced drop by drop, while adjusting the temperature of the oil bath of the evaporator in such a way that the distillation of the solvent is instantaneous. After introduction of all of the solution, the impregnated and dried support is transferred under nitrogen into a tubular reactor in order to there undergo a thermal treatment analogous to the one described in Example 1. Analysis indicates that the respective palladium and molybdenum concentrations in the obtained catalyst amount to 2.5% and 2.7%.

EXAMPLE 5

10 g of nitrobenzene, 1 g of pyridine, 1.8 g of the catalyst prepared in Example 4 are introduced into the autoclave used in Example 2 and the total volume is made up to 100 ml with ortho-dichlorobenzene. After flushing with nitrogen, carbon monoxide is compressed to a pressure of 100 bars and then the reactor is insulated and heated to 240° C. under agitation for 70 minutes. Cooling is allowed to take place and the mixture is analyzed. The overall conversion rate is 100% and the phenylisocyanate selectivity is 71.5%.

EXAMPLE 6

(THIS IS A COMPARATIVE EXAMPLE)

3.7 g of alumina identical to the one used in Example 1 and crushed into grains of 200 to 600 μm are placed into a spherical flask mounted on a rotary evaporator. Into the spherical flask having been flushed with nitrogen 60 ml of an aqueous ammoniacal solution containing 0.42 g of palladium acetate and 0.18 g of ammonium molybdate are poured. The water is distilled under reduced pressure and, after drying, the impregnated support is placed into a firing tube in order to there undergo a thermal treatment analogous to the one described in Example 1. Analysis indicates that the catalyst having thus been prepared contains 3.4% of palladium and 1.7% of molybdenum.

1.8 g of this catalyst as well as 10 g of nitrobenzene and 1 g of pyridine are charged into the autoclave used in Example 2 and the volume is made up to a total volume of 100 ml with the addition of ortho-dichlorobenzene. By operating in an identical fashion with Example 2 at 240° C. under 200 bars of carbon monoxide at 20° C., a T.T.G. (overall conversion rate) of nitrobenzene of 100% and a phenylisocyanate selectivity of 62% are obtained.

EXAMPLE 7

Utilizing the same procedure as set forth in Example 1, 4 g of commercial alumina, having a particle granulometry of between 200 and 600 μm and a specific surface of 350 m²/g, are impregnated with a solution of 1.07 g of the mixed cluster $Pd_2Cr_2(\eta^5-C_5H_5)_2(CO)_6(PPh_3)_2$ in methylene chloride. After heat treatment at 350° C., analysis indicates that the catalyst thus prepared contains 4% of palladium and 1.9% of chromium.

10 g of nitrobenzene, 2.1 g of the above catalyst, and 1 g of pyridine are placed into the autoclave and the total volume made up to 100 ml with the addition of ortho-dichlorobenzene. After introduction of carbon monoxide at 200 bars, the autoclave is heated to 200° C., under agitation, for 3 hours and to 240° C. for 1 hour and 20 minutes. Cooling is allowed to take place and the mixture is analyzed. The T.T.G. of nitrobenzene amounts to 90.8% and the phenylisocyanate selectivity to 65%.

EXAMPLE 8

Operating according to the method set forth in Example 1, 3 g of the alumina utilized in Example 7 are impregnated with a solution of 1 g of the mixed cluster $Pd_2W_2(\eta^5-C_5H_5)_2(CO)_6(PPh_3)_2$ in methylene chloride. After heat treatment at 350° C., the respective palladium and tungsten concentrations in the catalyst amount to 3.6% and 6.2%.

10 g of nitrobenzene, 2.1 g of the above catalyst, and 1 g of pyridine are placed into the autoclave and the total volume made up to 100 ml with the addition of ortho-dichlorobenzene. There is introduced into the autoclave carbon monoxide at a pressure of 200 bars and the autoclave heated at 240° C., under agigation. After 1 hour and 20 minutes, cooling is allowed to take place and the mixture is analyzed. The T.T.G. of nitrobenzene amounts to 100% and the phenylisocyanate selectivity to 56%.

EXAMPLE 9

Using the method set forth in Example 1, 4 g of an alumina support identical to that utilized in example 7 are impregnated with a solution of 0.8 of the mixed cluster $Pt_2W_2(\eta^5-C_5H_5)_2(CO)_6(PPh_3)_2$ in methylene chloride. After heat treatment at 350° C., analysis indicates that the catalyst thus prepared contains 4% of platinum and 3.7% of tungsten.

10 g of nitrobenzene, 3 g of the above catalyst, and 1 g of pyridine are placed into the autoclave and the total volume made up to 100 ml with the addition of ortho-dichlorobenzene. After introduction of carbon monoxide at a pressure of 200 bars, the autoclave is heated at 240° C., under agitation for 3 hours and 15 minutes, then allowed to cool. The mixture is analyzed and it is found that the T.T.G. of nitrobenzene amounts to 96% and the phenylisocyanate selectivity to 57%.

While the invention has been described in connection with a preferred embodiment, it is not intended to limit the scope of the invention to the particular form set forth, but, on the other hand, it is intended to cover such alternatives, modifications, and equivalents as may be included within the spirit and scope of the invention as defined by the appended claims.

What is claimed is:

1. In the process for the manufacture of aromatic isocyanates by carbonylation of nitro derivatives, the improvement comprising carrying out the reaction in the presence of a supported catalyst comprising as the active phase particles or an oxide of a precious metal of Group VIII and of a metal selected from Group $V_B$, $VI_B$, or VIII of the Periodic Table; and precursor of the active phase being a heteropolymetallic cluster.

2. The process of claim 1 wherein the heteropolymetallic cluster is a mixed bimetallic cluster.

3. The process of claim 2 wherein the catalyst is impregnated with a solution of the heteropolymetallic cluster and the thus impregnated support is subjected to a thermal treatment prior to the use of the catalyst.

4. The process of claims 1, 2, or 3 wherein the concentration by weight of the metals on the support is between 0.1 and 20% of the weight of the supported catalyst.

5. The process of claims 1, 2, or 3 wherein the catalyst is used in a reaction medium containing pyridine as solvent.

6. The process according to claims 1, 2, or 3 wherein the catalyst is in a reaction medium whose CO pressure at 20° C. is between 20 and 500 bars.

7. The process according to claims 1, 2, or 3 wherein the catalyst is in a reaction medium whose temperature is between 100° and 500° C.

* * * * *